United States Patent [19]
DeLuca et al.

[11] Patent Number: 5,578,587
[45] Date of Patent: Nov. 26, 1996

[54] METHODS AND COMPOSITIONS CONTAINING VITAMIN D COMPOUNDS FOR IMPROVEMENT OF SKIN CONDITIONS

[75] Inventors: Hector F. DeLuca, Deerfield; Connie M. Smith, Madison, both of Wis.

[73] Assignee: Wisconsin Alumni Research Foundation, Madison, Wis.

[21] Appl. No.: 396,637

[22] Filed: Mar. 1, 1995

Related U.S. Application Data

[62] Division of Ser. No. 971,669, Nov. 4, 1992, Pat. No. 5,459,136, which is a continuation of Ser. No. 573,560, Aug. 24, 1990, abandoned.

[51] Int. Cl.$^6$ .................................................... A61K 31/59
[52] U.S. Cl. ........................... 514/167; 552/653; 514/844
[58] Field of Search ..................................... 514/167, 844; 552/653

[56] References Cited

U.S. PATENT DOCUMENTS

| Re. 33,107 | 11/1989 | Dikstein et al. | 514/46 |
|---|---|---|---|
| 4,610,978 | 9/1986 | Dikstein et al. | 514/46 |
| 4,717,721 | 1/1988 | DeLuca et al. | 514/167 |
| 4,728,643 | 3/1988 | Holick et al. | 514/167 |
| 4,800,198 | 1/1989 | DeLuca et al. | 514/167 |
| 4,847,012 | 7/1989 | DeLuca et al. | 260/397 |
| 4,851,401 | 7/1989 | DeLuca et al. | 514/167 |
| 4,853,378 | 8/1989 | Hamma et al. | 514/167 |
| 4,927,815 | 5/1990 | DeLuca et al. | 514/167 |
| 4,940,700 | 7/1990 | DeLuca et al. | 514/167 |
| 5,087,619 | 2/1992 | Baggiolini et al. | 514/167 |

FOREIGN PATENT DOCUMENTS

| 0129003 | 3/1983 | European Pat. Off. . |
|---|---|---|
| 0387077 | 3/1989 | European Pat. Off. . |
| 62-169711 | 7/1987 | Japan . |
| WOA89/10351 | 11/1989 | WIPO . |

OTHER PUBLICATIONS

Perlman et al, Tetrahedron Letters, 1990, vol. 31, No. 13, pp. 1823–1824.

Kutner et al, The Journal of Organic Chemistry, 1988, vol. 53, pp. 3450–3457.

*Primary Examiner*—Theodore J. Criares
*Attorney, Agent, or Firm*—Andrus Sceales Starke & Sawall

[57] ABSTRACT

Compositions containing one or more Vitamin D compounds selected from the group consisting of 1α-hydroxyvitamin D homolog compouns, 19-nor-vitamin C compounds and secosterol compounds useful in the treatment of various skin conditions.

8 Claims, 7 Drawing Sheets

METHODS AND COMPOSITIONS CONTAINING VITAMIN D COMPOUNDS FOR IMPROVEMENT OF SKIN CONDITIONS

This invention was made with United States Government support awarded by the National Institute of Health (NIH), Grant No. DK-14881. The United States Government has certain rights in this invention.

This application is a divisional of application Ser. No. 07/971,669 filed Nov. 4, 1992, now U.S. Pat. No. 5,459,136, which in turn is a continuation of application Ser. No. 07/573,560 filed Aug. 24, 1990, now abandoned.

BACKGROUND OF THE INVENTION

The present invention relates to cosmetic compositions, and more particularly to such compositions containing vitamin D compounds.

Skin problems range between severe skin disorders such as dermatitis, eczema, psoriasis, solar keratosis and the like, and less severe skin conditions such as wrinkles, lack of dermal hydration i.e. dry skin, lack of adequate skin firmness i.e. skin slackness, insufficient sebum secretion and the like. The former skin disorders have typically been treated with compositions termed "dermatological" whereas the latter skin conditions have typically been treated with compositions termed "cosmetic" since the primary functions of such compositions are to preserve, condition or protect the skin.

In the past, treatment of various skin disorders and, skin conditions has been largely based on non-specific-drugs. For example, dermatitis has been commonly treated with corticosteroids. Such compounds may provide symptomatic relief for some patients. However, steroids are known to produce numerous local and systemic side effects, and their long term use is not recommended.

Holick et al U.S. Pat. No. 4,728,643 discloses a method of treating peoriasis by administering to a patient a vitamin D compound capable of differentiating cultured tumor cells. Examples of such compounds are vitamins $D_2$ or $D_3$ or derivatives of vitamins $D_2$ or $D_3$.

Dikstein et al U.S. Pat. No. 4,610,978 and U.S. Pat. No. Re. 33,107 disclose cosmetic and dermatological compositions containing 1 alphahydroxycholecalciferol or 1 alpha, 25-dihydroxycholecalciferol. These compositions are disclosed for use in the topical treatment of skin disorders and skin conditions such as dermatitis, psoriasis, eczema, solar keratosis, wrinkles, dry skin and skin slackness.

Japanese published patent application No. 62/169711 entitled "A Skin Cosmetic Material" discloses a skin cosmetic composition containing vitamin $D_3$ or vitamin $D_3$ derivatives. The vitamin $D_3$ derivatives disclosed include 25-hydroxycholecalciferol, 1 alpha-hydroxy-cholecalciferol, 5,6-trans-25-hydroxycholecalciferol, 1 alpha-25-dihydroxycholecalciferol and dihydrotachysterol.

Finally, DeLuca et al U.S. Pat. No. 4,800,198 discloses the structure of the secosterol compounds of interest in the present compositions. However, the patent is directed toward a method for inducing the differentiation of malignant cells utilizing secosterol compounds, and in particular to the treatment of leukemoid diseases with such compounds. The patent does not teach or suggest any cosmetic uses for the secosterol compounds disclosed therein.

SUMMARY OF THE INVENTION

Compositions containing one or more vitamin D compounds selected from the group consisting of 1α-hydroxyvitamin D homolog compounds, 19-nor-vitamin D compounds and secosterol compounds together with a suitable carrier useful in the treatment of various skin conditions are described. The treatment may be topical, oral or parenteral. Methods of employing the compositions are also disclosed. The compounds are present in the composition in an amount from about 0.001 μg/gm to about 10 μg/gm of the composition, and may be administered orally or parenterally in dosages of from about 0.1 μg/day to about 25 μg/day.

In one aspect of the invention, cosmetic compositions containing one or more side chain unsaturated 1α-hydroxyvitamin D homolog compounds for the treatment of skin conditions such as wrinkles, lack of dermal hydration i.e. dry skin, lack of adequate skin firmness i.e. slack skin, and insufficient sebum secretion are provided. Methods employing these compositions are also provided.

In another aspect of the invention, compositions containing one or more side chain saturated 1α-hydroxyvitamin D homolog compounds for the treatment of skin conditions such as wrinkles, lack of dermal hydration i.e. dry skin, lack of adequate skin firmness i.e. slack skin, and insufficient sebum secretion are provided. Methods employing these compositions are also provided.

In still another aspect of the invention, compositions containing one or more 19-nor-vitamin D compounds for the treatment of skin conditions such as wrinkles, lack of dermal hydration i.e. dry skin, lack of adequate skin firmness i.e. slack skin, and insufficient sebum secretion are provided. Methods employing these compositions are also provided.

In yet another aspect of the invention, compositions containing one or more secosterol compounds for the treatment of skin conditions such as wrinkles, lack of dermal hydration i.e. dry skin, lack of adequate skin firmness i.e. slack skin, and insufficient sebum secretion are provided. Methods employing these compositions are also provided.

Various formulations for the compositions are also provided. Such formulations may include creams, lotions, ointments, and the like. The compositions and/or formulations may also include additional active ingredients if desired.

The compounds disclosed herein unexpectedly provide highly effective treatments for the above skin conditions without producing unwanted systemic or local side effects.

DETAILED DESCRIPTION OF THE INVENTION

Figure 1:
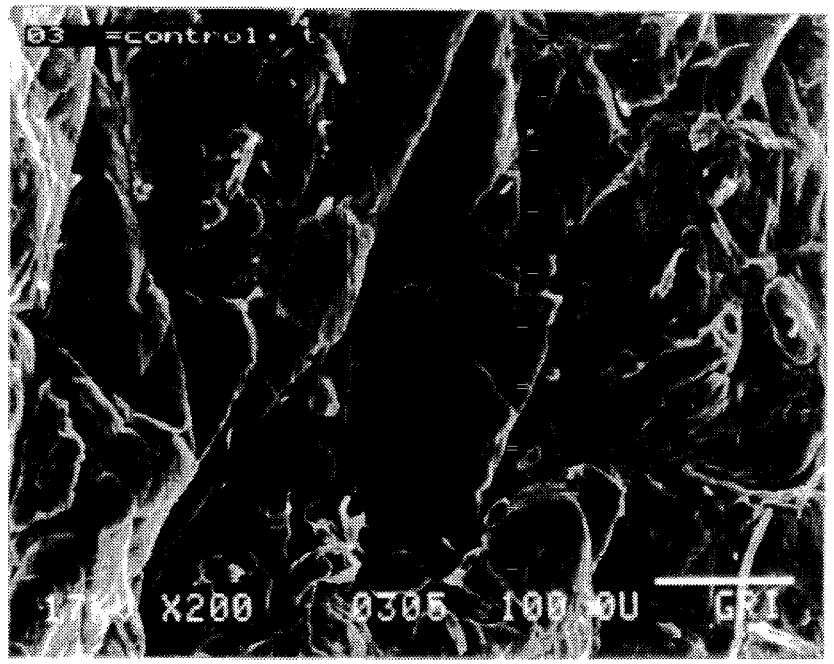
FIG. 1 is a photomicrograph at X200 magnification of a skin replica of a control mouse treated topically with a propylene glycol control vehicle.

It has now been found that effective treatment of various skin conditions can be achieved with compositions which include an effective amount of a vitamin D compound selected from the group consisting of 1α-hydroxyvitamin D homolog compounds, 19-nor vitamin D compounds and secosterol compounds together with a suitable carrier.

The 1α-hydroxyvitamin D homolog compounds useful in the compositions of the present invention are characterized structurally as side chain unsaturated and side chain saturated homologs of vitamin D, and preferably of 1,25-$(OH)_2D_3$ in which the side chain is elongated by insertion of one or more methylene units into the chain at the carbon 24 position. They may be represented, therefore, by the following general structure of formula I:

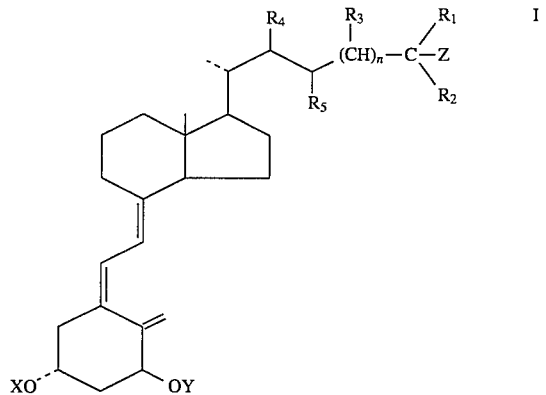

where $R_4$ and $R_5$ represent hydrogen or when taken together $R_4$ and $R_5$ represent a carbon-carbon double bond or a carbon-carbon triple bond, Z represents hydrogen, hydroxy or protected-hydroxy, $R_3$ represents hydrogen, hydroxy, protected hydroxy or an alkyl group, X and Y which may be the same or different are hydrogen or a hydroxy-protecting group, $R_1$ represents the group —$(CH_2)_q$—H and $R_2$ represents the group —$(CH_2)_p$—H, and where n, q and p are integers having independently the values of 1 to 5 with the proviso that at least one of n, q and p is greater than 1, and $R_1$ and $R_2$ when taken together represent the group —$(CH_2)_m$— where m is an integer having the value of 2 to 5.

The 19-nor-vitamin D compounds referred to herein are a class of 1α-hydroxylated vitamin D compounds in which the ring A exocyclic methylene group (carbon 19) typical of all vitamin D systems has been removed and replaced by two hydrogen atoms. Structurally these novel analogs are characterized by the general formula II shown below:

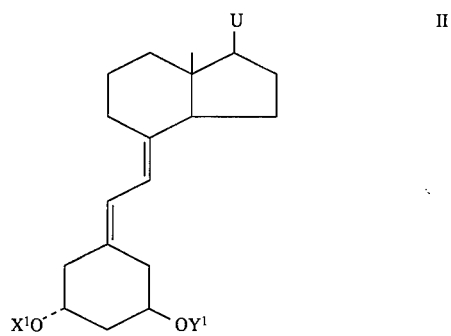

where $X^1$ and $Y^1$ are each selected from the group consisting of hydrogen, acyl, alkylsilyl and alkoxyalkyl, and where the group U represents any of the typical side chains known for vitamin D compounds. Thus, U may be an alkyl, hydrogen, hydroxyalkyl or fluoroalkyl group, or U may represent the following side chain:

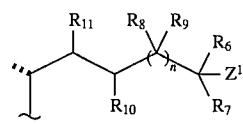

wherein $Z^1$ represents hydrogen, hydroxy or O-acyl, $R_6$ and $R_7$ are each selected from the group consisting of alkyl, hydroxyalkyl and fluoroalkyl, or, when taken together represent the group —$(CH_2)_m$—where m is an integer having a value of from 2 to 5, $R_8$ is selected from the group consisting of hydrogen, hydroxy, fluorine, O-acyl, alkyl, hydroxyalkyl and fluoroalkyl, $R_9$ is selected from the group consisting of hydrogen, fluorine, alkyl, hydroxyalkyl and fluoroalkyl, or, $R_8$ and $R_9$ taken together represent double-bonded oxygen or double-bonded carbon, $R_{10}$ and $R_{11}$ are each selected from the group consisting of hydrogen, hydroxy, O-acyl, fluorine and alkyl, or, $R_{10}$ and $R_{11}$ taken together form a carbon-carbon double bond or a carbon-carbon triple bond, and wherein n is an integer having a value of from 1 to 5, and wherein the carbon at any one of positions 20, 22, or 23 in the side chain may be replaced by an O, S, or N atom.

Specific important examples of side chains for the 19-nor compounds are the structures represented by formulas (a), (b), (c), (d) and (e) below, i.e. the side chain as it occurs in 25-hydroxyvitamin $D_3$ (a); vitamin $D_3$ (b); 25-hydroxyvitamin $D_2$ (c); vitamin $D_2$ (d); and the C-24-epimer of 25-hydroxyvitamin $D_2$ (e).

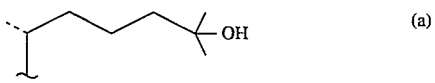

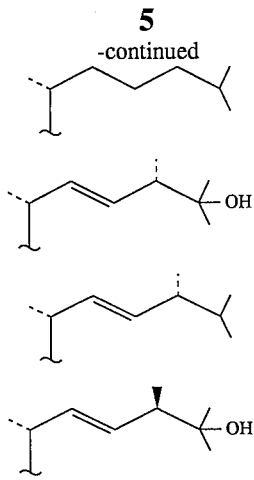

Purely structurally, the class of secosterol compounds referred to herein has a similarity with some of the known vitamin D compounds. Unlike the known vitamin D compounds, however, the secosterols used in the present invention do not express the classic vitamin D activities in vivo, i.e. stimulation of intestinal calcium transport, or the mobilization of bone calcium, and hence they cannot be classified as vitamin D derivatives from the functional point of view. In light of the prior art, it was all the more surprising and unexpected then, to find that these secosterols are remarkably effective in the treatment of skin conditions. This finding provides an effective method for the treatment of skin conditions, since the above described secosterols can be administered to subjects in doses sufficient to treat the skin condition, without producing simultaneously unphysiologically high and deleterious blood calcium levels.

The group of secosterols exhibiting this unique and heretofore unrecognized activity pattern is characterized by the general structure III shown below:

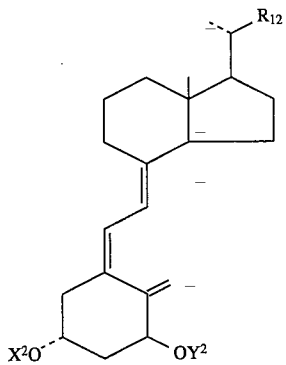

where $R_{12}$ is hydrogen, methyl, ethyl or propyl and where each of $X^2$ and $Y^2$ represent, independently, hydrogen, an acyl group, or a hydroxy-protecting group.

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. An acyl group is an alkanoyl group of 1 to 6 carbons in all its isomeric forms, or an aroyl group, such as benzoyl, or halo-, nitro- or alkyl-substituted benzoyl groups, or a dicarboxylic acyl group such as oxalyl, malonyl, succinoyl, glutaroyl, or adipoyl. The term "aryl" signifies a phenyl-, or an alkyl-, nitro- or halo-substituted phenyl group.

It should be noted in this description that the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R_1$ and $R_2$ are ethyl groups. Likewise, the term "26,27-diethyl" refers to the addition of an ethyl group at the 26 and 27 positions so that $R_1$ and $R_2$ are propyl groups.

Specific and preferred examples of these compounds when the side chain is unsaturated (i.e. $R_4$ and $R_5$ represent a double bond) are: 24-dihomo-1,25-dihydroxy-22-dehydrovitamin $D_3$, i.e. the compound shown above, where X and Y are hydrogen, Z is hydroxy, n equals 3, and $R_1$ and $R_2$ are each a methyl group; 26,27-dimethyl-24-dihomo-1,25-dihydroxy-22-dehydrovitamin $D_3$, i.e. the compound shown above where X and Y are hydrogen, Z is hydroxy, n equals 3, and $R_1$ and $R_2$ are each an ethyl group; 24-trihomo-1,25-dihydroxy-22-dehydrovitamin $D_3$, i.e. the compound having the structure shown above, where X and Y are hydrogen, Z is hydroxy, n equals 4, and $R_1$ and $R_2$ are each a methyl group; 26,27-dimethyl-24-trihomo-1,25-dihydroxy-22-dehydrovitamin $D_3$, i.e. the compound shown above where X and Y are hydrogen, Z is hydroxy, n equals 4, and $R_1$ and $R_2$ are each an ethyl group; 26,27-diethyl-24-dihomo-1,25-dihydroxy-22-dehydrovitamin $D_3$, i.e. the compound shown above where X and Y are hydrogen, Z is hydroxy, n equals 3, and $R_1$ and $R_2$ are each a propyl group; 26,27-diethyl-24-trihomo-1,25-dihydroxy-22-dehydrovitamin $D_3$, i.e. the compound shown above where X and Y are hydrogen, Z is hydroxy, n equals 4, and $R_1$ and $R_2$ are each a propyl group, 26,27-dipropyl-24-dihomo-1,25-dihydroxy-22-dehydrovitamin $D_3$, i.e. the compound shown above where X and Y are hydrogen, Z is hydroxy, n equals 3, and $R_1$ and $R_2$ are each a butyl group; and 26,27-dipropyl-24-trihomo-1, 25-dihydroxy-22-dehydrovitamin $D_3$, i.e. the compound shown above where X and Y are hydrogen, Z is hydroxy, n equals 4, and $R_1$ and $R_2$ are each a butyl group.

Specific and preferred examples of these compounds when the side chain is saturated (i.e. $R_4$ and $R_5$ each represent hydrogen) are: 24-dihomo-1,25-dihydroxy-vitamin $D_3$, i.e. the compound shown above, where X and Y are hydrogen, Z is hydroxy, n equals 3, and $R_1$ and $R_2$ are each a methyl group; 26,27-dimethyl-24-dihomo-1,25-dihydroxy-vitamin $D_3$, i.e. the compound shown above where X and Y are hydrogen, Z is hydroxy, n equals 3, and $R_1$ and $R_2$ are each an ethyl group; 24-trihomo-1, 25-dihydroxy-vitamin $D_3$, i.e. the compound having the structure shown above, where X and Y are hydrogen, Z is hydroxy, n equals 4, and $R_1$ and $R_2$ are each a methyl group; 26,27-dimethyl-24-trihomo-1,25-dihydroxy-vitamin $D_3$, the compound shown above where X and Y are hydrogen, Z is hydroxy, n equals 4, and $R_1$ and $R_2$ are each an ethyl group; 26,27-diethyl-24-dihomo-1,25-dihydroxy-vitamin $D_3$, i.e. the compound shown above where X and Y are hydrogen, Z is hydroxy, n equals 3, and $R_1$ and $R_2$ are each a propyl group; 26, 27-diethyl-24-trihomo-1,25-dihydroxy-vitamin $D_3$, i.e. the compound shown above where X and Y are hydrogen, Z is hydroxy, n equals 4, and $R_1$ and $R_2$ are each a propyl group; 26,27-dipropyl-24-dihomo-1,25-dihydroxy-vitamin $D_3$, i.e. the compound shown above where X and Y are hydrogen, Z is hydroxy, n equals 3, and $R_1$ and $R_2$ are each a butyl group; and 26,27-dipropyl-24-trihomo-1,25-dihydroxy-vitamin $D_3$, i.e. the compound shown above where X and Y are hydrogen, Z is hydroxy, n equals 4, and $R_1$ and $R_2$ are each a butyl group.

Preparation of Homologated Saturated And Unsaturated Side Chain Compounds

Examples of the compounds of this invention wherein the side chain is saturated can be prepared according to the general process illustrated and described in U.S. Pat. No. 4,927,815 issued May 22, 1990 entitled "Compounds Effective In Inducing Cell differentiation And Process For Preparing Same," the description of which is specifically incorporated herein by reference. Examples of the compounds of this invention wherein the side chain is unsaturated can be prepared according to the general process illustrated and described in U.S. Pat. No. 4,847,012 issued Jul. 11, 1989 entitled "Vitamin D Related Compounds And Processes For Their Preparation," the description of which is specifically incorporated herein by reference. Examples of the compounds of this invention wherein $R_1$ and $R_2$ together represent a cyclopentano group can be prepared according to the general process illustrated and described in U.S. Pat. No. 4,851,401 issued Jul. 25, 1989 entitled "Novel Cyclopentano-Vitamin D Analogs," the description of which is specifically incorporated herein by reference.

Another synthetic strategy for the preparation of side-chain-modified analogues of 1α,25-dihydroxyergocalciferol is disclosed in Kutner et al, *The Journal of Organic Chemistry*, 1988, Vol. 53, pages 3450–3457. In addition, the preparation of 24-homo and 26-homo vitamin D analogs are disclosed in U.S. Pat. No. 4,717,721 issued Jan. 5, 1988 entitled "Sidechain Homo-Vitamin D Compounds With Preferential Anti-Cancer Activity" the description of which is specifically incorporated herein by reference.

Preparation of 19-Nor-Vitamin D Compounds

The preparation of 1α-hydroxy-19-nor-vitamin D compounds having the basic structure shown above in formula II can be accomplished by a common general method, using known vitamin D compounds as starting materials. For the synthesis of 1α,25-dihydroxy-19-nor-vitamin $D_3$, reference is made to Perlman et al, *Tetrahedron Letters*, 1990, Vol. 31, No. 13, pages 1823–1824. Suitable starting materials are, for example, the vitamin D compounds of the general structure IV:

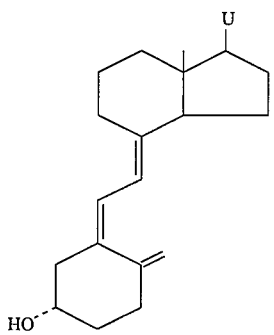

IV where U is any of the side chains as defined above. These vitamin D starting materials are known compounds, or compounds that can be prepared by known methods.

Using the procedure of DeLuca et al U.S. Pat. No. 4,195,027, the starting material is converted to the corresponding 1α-hydroxy-3,5-cyclovitamin D derivative, having the general structure V below, where $X^3$ represents hydrogen and Q represents an alkyl, preferably methyl:

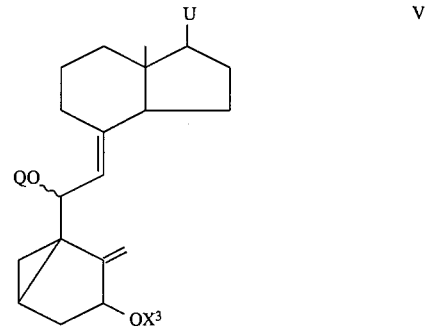

V

So as to preclude undesired reaction of the 1α-hydroxy group in subsequent steps, the hydroxy group is converted to the corresponding acyl derivative, i.e. the compound V shown above, where $X^3$ represents an acyl group, using standard acylation procedures, such as treatment with an acyl anhydride or acyl halide in pyridine at room temperature or slightly elevated temperature (30°–70° C.). It should be understood also that whereas the process of this invention is illustrated here with acyl protection of hydroxy functions, alternative standard hydroxy-protecting groups can also be used, such as, for example, alkylsilyl or alkoxyalkyl groups. Such protecting groups are well-known in the art (e.g. trimethylsilyl, triethylsilyl, t.-butyldimethylsilyl, or tetrahydrofuranyl, methoxymethyl), and their use is considered a routine modification of experimental detail within the scope of the process of this invention.

The derivative as obtained above is then reacted with osmium tetroxide, to produce the 10,19-dihydroxy analog, VI (where $X^3$ is acyl), which is subjected to diol cleavage using sodium metaperiodate or similar vicinal diol cleavage reagents (e.g. lead tetraacetate) to obtain the 10-oxo-intermediate, having the structure VII below (where $X^3$ is acyl):

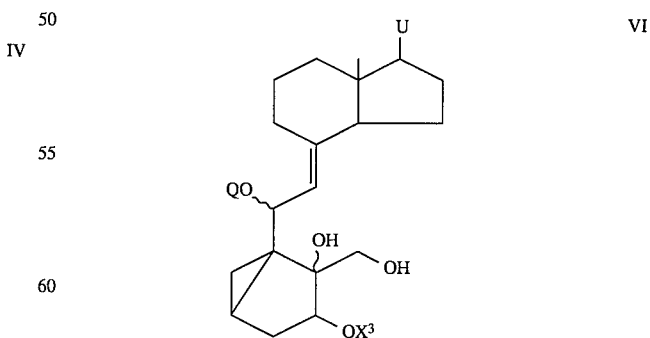

VI

-continued

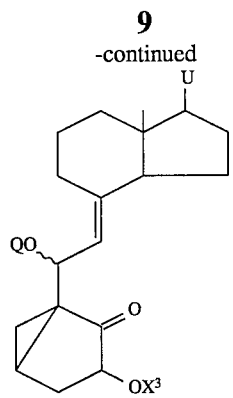

VII

These two consecutive steps can be carried out according to the procedures given by Paaren et al. (J. Org. Chem. 48, 3819 (1983)). If the side chain unit, U carries vicinal diols (e.g. 24,25-dihydroxy- or 25,26-dihydroxy, etc.), these, of course, also need to be protected, e.g. via acylation, silylation, or as the isopropylidene derivative prior to the periodate cleavage reactions.

In most cases, the acylation of the 1α-hydroxy group as mentioned above will simultaneously effect the acylation of side chain hydroxy functions, and these acylation conditions can, of course, be appropriately adjusted (e.g. elevated temperatures, longer reaction times) so as to assure complete protection of side chain vicinal diol groupings.

The next step of the process comprises the reduction of the 10-oxo-group to the corresponding 10-alcohol having the structure VIII shown below (where $X^3$ is acyl and $Y^3$ represents hydroxy). When $X^3$ is acyl, this reduction is carried out conveniently in an organic solvent at from about 0° C. to about room temperature, using $NaBH_4$ or equivalent hydride reducing agents, selective for the reduction of carbonyl groups without cleaving ester functions. Obviously, when $X^3$ is a hydroxy-protecting group that is stable to reducing agents, any of the other hydride reducing agents (e.g. $LiAlH_4$, or analogous reagents) may be employed also.

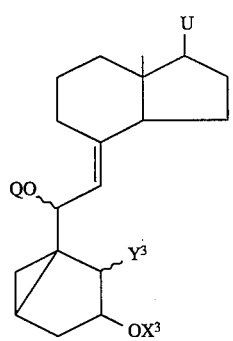

VIII

The 10-hydroxy intermediate is then treated with an alkyl-or arylsulfonylhalide (e.g. methanesulfonylchloride) in a suitable solvent (e.g. pyridine) to obtain the corresponding 10-O-alkyl-or arylsulfonyl derivative (the compound having the structure shown VIII above, where $Y^3$ is alkyl-$SO_2O$—, or aryl-$SO_2O$—, and this sulfonate intermediate is then directly reduced, with lithium aluminum hydride, or the analogous known lithium aluminum alkyl hydride reagents in an ether solvent, at a temperature ranging from 0° C. to the boiling temperature of the solvent, thereby displacing the sulfonate group and obtaining the 10-deoxy derivative, represented by the structure VIII above, where $X^3$ and $X^3$ are both hydrogen. As shown by the above structure, a 1-O-acyl function in the precursor compound VII is also cleaved in this reduction step to produce the free 1α-hydroxy function, and any O-acyl protecting group in the side chain would, of course, likewise be reduced to the corresponding free alcohol function, as is well understood in the art. If desired, the hydroxy groups at C-1 (or hydroxy groups in the side chain) can be reprotected by acylation or silylation or ether formation to the corresponding acyl, alkylsilyl or alkoxyalkyl derivative, but such protection is not required. Alternative hydroxy-protecting groups, such as alkylsilyl or alkoxyalkyl groups would be retained in this reduction step, but can be removed, as desired, at this or later stages in the process by standard methods known in the art.

The above 1α-hydroxy-10-deoxy cyclovitamin D intermediate is next solvolyzed in the presence of a low-molecular weight organic acid, using the conditions of DeLuca et al U.S. Pat. Nos. 4,195,027 and 4,260,549. When the solvolysis is carried out in acetic acid, for example, there is obtained a mixture of 1α-hydroxy-19-nor-vitamin D 3-acetate and 1α-hydroxy-19-nor-vitamin D 1-acetate (compounds IX and X, below), and the analogous 1- and 3-acylates are produced, when alternative acids are used for solvolysis.

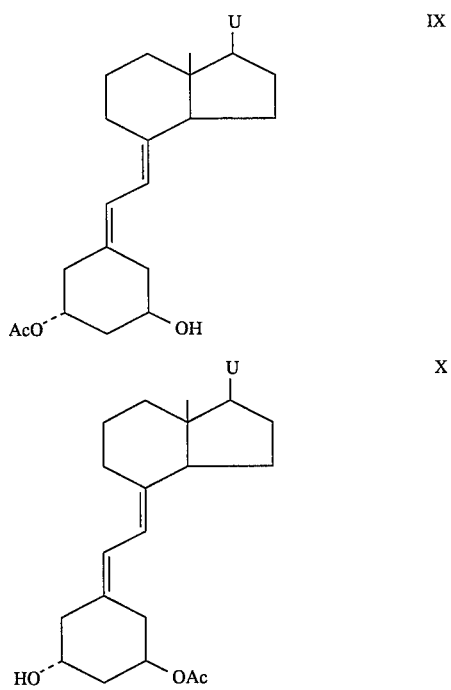

Direct basic hydrolysis of this mixture under standard conditions then produces the desired 1α-hydroxy-19-nor-vitamin D compounds of structure II above (where $X^1$ and $Y^1$ are both hydrogen). Alternatively, the above mixture of monoacetates may also be separated (e.g. by high pressure liquid chromatography) and the resulting 1-acetate and 3-acetate isomers may be subjected separately to hydroxysis to obtain the same final product from each, namely the 1α-hydroxy-19-nor-vitamin D compounds of structure II. Also the separated monoacetates of structure IX or X or the free 1,3-dihydroxy compound can, of course, be reacylated according to standard procedures with any desired acyl group, so as to produce the product of structure II above, where $X^1$ and $Y^1$ represent acyl groups which may be the same or different.

The 19-nor-vitamin D compounds useful in this invention are more specifically described by the following illustrative examples. In these examples specific products identified by Roman numerals and letters, i.e. IIa, IIb, . . . , etc. refer to the specific structures and side chain combinations identified in the preceding description.

EXAMPLE 1

Preparation of 1α,25-dihydroxy-19-nor-vitamin $D_3$ (IIa)

(a) 1α, 25-Dihydroxy-3,5-cyclovitamin $D_3$ 1-acetate, 6-methyl ether: Using 25-hydroxyvitamin $D_3$ (IVa) as starting material, the known 1α, 25-dihydroxy-3,5-cyclovitamin derivative Va ($X^3$=H) was prepared according to published procedures (DeLuca et al., U.S. Pat. No. 4,195,027 and Paaren et al., J. Org. Chem. 45, 3252 (1980)). This product was then acylated under standard conditions to obtain the corresponding 1-acetate derivative Va ($X^3$=Ac).

(b) 10,19-Dihydro-1α,10,19,25-tetrahydroxy-3,5-cyclovitamin $D_3$ 1-acetate, 6-methyl ether (VIa): Intermediate Va ($X^3$=Ac) was treated with a slight molar excess of osmium tetroxide in pyridine according to the general procedure described by Paaren et al. (J. Org. Chem. 48., 3819 (1983)) to obtain the 10,19-dihydroxylated derivative VIa. Mass spectrum m/z (relative intensity), 506 ($M^+$, 1), 488 (2), 474 (40), 425 (45), 396 (15), 285 (5), 229 (30), 133 (45), 59 (80), 43 (100). $^1$H, NMR (CDCl$_3$) δ0.52 (3H, s, 18-CH$_3$, 0.58 (1H, m, 3-H), 0.93 (3H, d, J=6.1 Hz, 21-CH$_3$, 1.22 (6H, s, 26-CH$_3$ and 27-CH$_3$), 2.10 (3H, s, COCH$_3$), 3.25 (3H, s, 6-OCH$_3$ 3.63 (2H, m, 19-CH$_2$), 4.60 (1H, d, J=9.2 Hz, 6-H), 4.63 (1H, dd, 1β-H), 4.78 (1H, d, J=9.2 Hz, 7-H).

(c) 1α,25-Dihydroxy-10-oxo-3,5-cyclo-19-nor-vitamin $D_3$ 1-acetate, 6-methyl ether (VIIa): The 10,19-dihydroxylated intermediate VIa was treated with a solution of sodium metaperiodate according to the procedure given by Paaren et al. (J. Org. Chem. 48, 3819, 1983) to produce the 10-oxo-cyclovitamin D derivative (VIIa, $X^3$=Ac). Mass spectrum m/z (relative intensity) 442 ($M^+$-MeOH) (18), 424 (8), 382 (15), 364 (35), 253 (55), 225 (25), 197 (53), 155 (85), 137 (100). $^1$H NMR (CDCl$_3$) δ0.58 (3H, s, 18-CH$_3$), 0.93 (3H, d, J=6.6 Hz, 21-CH$_3$), 1.22 (6H, s, 26-CH$_3$ add 27-CH$_3$), 2.15 (s, 3-OCOCH$_3$), 3.30 (3H, s, 6-OCH$_3$), 4.61 (1H, d, J=9.1 Hz, 6-H), 4.71 (1H, d, J=9.6 Hz, 7-H), 5.18 (1H,m, 1β-H).

It has been found also that this diol cleavage reaction does not require elevated temperatures, and it is, indeed, generally preferable to conduct the reaction at approximately room temperature.

(d) 1α-Acetoxy-10,25-dihydroxy-3,5-cyclo-19-nor-vitamin $D_3$ 6-methyl ether (VIIIa, $X^3$=Ac, $Y^3$=OH): The 10-oxo derivative VIIa ($X^3$=Ac) (2.2 mg, 4.6 μmol) was dissolved in 0.5 ml of ethanol and to this solution 50 μl (5.3 μmol) of a NaBH$_4$ solution (prepared from 20 mg of NaBH$_4$, 4.5 ml water and 0.5 ml of 0.01N NaOH solution) was added and the mixture stirred at 0° C. for ca. 1.5 h, and then kept at 0° C. for 16 h. To the mixture ether was added and the organic phase washed with brine, dried over MgSO$_4$, filtered and evaporated. The crude product was purified by column chromatography on a 15×1 cm silica gel column and the alcohol VIIIa ($X^3$=Ac, $Y^3$=OH) was eluted with ethyl acetate hexane mixtures to give 1.4 mg (3 μmol) of product. Mass spectrum m/z (relative intensity) 476 ($M^+$) (1), 444 (85), 426 (12), 384 (30), 366 (48), 351 (21), 255 (35), 237 (48), 199 (100), 139 (51), 59 (58).

(e) 1α,25-Dihydroxy-19-nor-vitamin $D_3$ (IIa, $X^1$=$Y^1$=H): The 10-alcohol (VIIIa, $X^3$=Ac, $Y^3$=OH) (1.4 mg) was dissolved in 100 μl anhydrous CH$_2$Cl$_2$ and 10 μl (14 μmol) triethylamine solution (prepared from 12 mg (16 μl) triethylamine in 100 μl anhydrous CH$_2$Cl$_2$), followed by 7 μl (5.6 μmol) methyl chloride solution (9 mg mesyl chloride, 6.1 μl, in 100 μl anhydrous CH$_2$Cl$_2$) added at 0° C. The mixture was stirred at 0° C. for 2 h. The solvents were removed with a stream of argon and the residue (comprising compound VIIIa $X^3$=Ac $Y^3$=CH$_3$SO$_2$O—) dissolved in 0.5 ml of anhydrous tetrahydrofuran; 5 mg of LiAlH$_4$ was added at 0° C. and the mixture kept at 0° C. for 16 h. Excess LiAlH$_4$ was decomposed with wet ether, the ether phase was washed with water and dried over MgSO$_4$, filtered and evaporated to give the 19-nor product VIIIa ($X^3$=$Y^3$=H).

This product was dissolved in 0.5 ml of acetic acid and stirred at 55° C. for 20 min. The mixture was cooled, ice water added and extracted with ether. The other phase was washed with cold 10% sodium bicarbonate solution, brine, dried over MgSO$_4$, filtered and evaporated to give the expected mixture of 3-acetoxy-1-α-hydroxy- and 1α-acetoxy-3-hydroxy isomers, which were separated and purified by HPLC (Zorbax Sil column, 6.4×25 cm, 2-propanol in hexane) to give about 70 μg each of compounds IXa and Xa. UV (in EtOH) $\lambda_{max}$ 242.5 (OD 0.72), 251.5 (OD 0.86), 260 (OD 0.57).

Both 19-nor-1,25-dihydroxyvitamin $D_3$ acetates IXa and Xa were hydrolyzed in the same manner. Each of the monoacetates was dissolved in 0.5 ml of ether and 0.5 ml 0.1N KOH in methanol was added. The mixture was stirred under argon atmosphere for 2 h. More ether was added and the organic phase washed with brine, dried over anhydrous MgSO$_4$, filtered and evaporated. The residue was dissolved in a 1:1 mixture of 2-propanol and hexane and passed through a Sep Pak column and washed with the same solvent. The solvents were evaporated and the residue purified by HPLC (Zorbax Sil, 6.4×25 cm, 10% 2-propanol in hexane). The hydrolysis products of IXa and Xa were identical and gave 66 μg of IIa ($X^1$=$Y^1$=H). Mass spectrum (mz relative intensity) 404 ($M^+$) (100), 386 (41), 371 (20), 275 (53), 245 (51), 180 (43), 135 (72), 133 (72), 95 (82), 59 (18), exact mass calcd. for C$_{26}$H$_{44}$O$_3$ 404.3290, found 404.3272. $^1$H NMR (CDCl$_3$) δ0.52 (3H, s, 18-CH$_3$), 0.92 (3H, d, J=6.9 Hz, 21-CH$_3$), 1.21 (6H, s, 26-CH$_3$ and 27-CH$_3$), 4.02 (1H, m, 3αH), 4.06 (1H, m, 1β-H), 5.83 (1H, d, J=11.6 Hz, 7-H), 6.29 (1H, d, J=10.7Hz, 6-H). UV (in EtOH), $\lambda_{max}$ 243 (OD 0.725), 251.5 (OD 0.823), 261 (OD 0.598).

EXAMPLE 2

Preparation of 1α-hydroxy-19-nor-vitamin $D_3$(IIb):

(a) With vitamin $D_3$ (IVb) as starting material, and utilizing the conditions of Example 1a, there is obtained known 1α-hydroxy-3,5-cyclovitamin $D_3$ 1-acetate, 6-methyl ether, compound Vb ($X^3$=Ac).

(b) By subjecting intermediate Vb ($X^3$=Ac), as obtained in Example 2a above to the conditions of Example 1b, there is obtained 10,19-dihydro-1α,10-19-trihydroxy-3,5-cyclovitamin $D_3$ 1-acetate, 6-methyl ether VIb ($X^3$=Ac).

(c) By treatment of intermediate VIb ($X^3$=Ac) with sodium metaperiodate according to Example 1c above, there is obtained 1α-hydroxy-10-oxo-3,5-cyclo-19-nor-vitamin $D_3$ 1-acetate, 6-methyl ether VIIb ($X^3$=Ac).

(d) Upon reduction of the 10-oxo-intermediate VIIb ($X^3$=Ac) under the conditions of Example 1d above, there is obtained 1α-acetoxy-10-hydroxy-3,5-cyclo-19-nor-vitamin $D_3$ 6-methyl ether VIIIb ($X^3$=Ac, $Y^3$=OH)(e)

(e) Upon processing intermediate VIIIb ($X^3$=Ac, $Y^3$=OH) through the procedure given in Example 1e above, there is obtained 1α-hydroxy-19-nor-vitamin $D_3$ (IIb, $X^1$=$Y^1$=H).

EXAMPLE 3

Preparation of 1α, 25-dihydroxy-19-nor-vitamin $D_2$ (a) Utilizing 25-hydroxyvitamin $D_2$ (IVc) as starting material and experimental conditions analogous to those of Example 1a, there is obtained 1α,25-dihydroxy-3,5-cyclovitamin $D_2$ 1-acetate, 6-methyl ether, compound Vc ($X^3$=Ac).

(b) Subjecting intermediate Vc ($X^3$=Ac), as obtained in Example 3a above, to the reaction conditions of Example 1b, provides 10,19-dihydro-1α,10,19,25-tetrahydroxy-3,5-cyclovitamin $D_2$ 1-acetate, 6-methyl ether, VIc ($X^3$=Ac).

(c) By treatment of intermediate VIc ($X^3$=Ac) with sodium metaperiodate according to general procedures of Example 1c above, there is obtained 1α,25-dihydroxy-10-oxo-3,5-cyclo-19-nor-vitamin $D_2$ 1 acetate, 6-methyl ether VIIc ($X^3$=Ac).

(d) Upon reduction of the 10-oxo-intermediate VIIc ($X^3$=Ac) under conditions analogous to those of Example 1d above, there is obtained 1α-acetoxy-10,25-dihydroxy-3,5-cyclo-19-nor-vitamin $D_2$ 6-methyl ether VIIIc ($X^3$=Ac, $Y^3$=OH).

(e) Upon processing intermediate VIIIc ($X^3$=Ac, $Y^3$=OH) through the procedural steps given in Example 1e above, there is obtained 1α,25-dihydroxy-19-nor-vitamin $D_2$ (IIc, $X^1$=$Y^1$=H).

EXAMPLE 4

Preparation of 1α-hydroxy-19-nor-vitamin $D_2$:

(a) With vitamin $D_2$ (IVd) as starting material, and utilizing the conditions of Example 1a, there is obtained known 1α-hydroxy-3,5-cyclovitamin $D_2$ 1-acetate, 6-methyl ether, compound Vd ($X^3$=Ac).

(b) By subjecting intermediate Vd ($X^3$=Ac), as obtained in Example 4a above to the conditions of Example 1b, there is obtained 10,19-dihydro-1α, 10,19-trihydroxy-3,5-cyclovitamin $D_2$ 1-acetate, 6-methyl ether, VId ($X^3$=Ac).

(c) By treatment of intermediate VId ($X^3$=Ac) with sodium metaperiodate according to Example 1c above, there is obtained 1α-hydroxy-10-oxo-3,5-cyclo-19-nor-vitamin $D_2$ 1-acetate, 6-methyl ether, VIId ($X^3$=Ac).

(d) Upon reduction of the 10-oxo-intermediate VIId ($X^3$=Ac) under the conditions of Example 1d above, there is obtained 1α-acetoxy-10-hydroxy-3,5-cyclo-19-nor-vitamin $D_2$ 6-methyl ether, VIIId ($X^3$=Ac, $Y^3$=OH).

(e) Upon processing intermediate VIIId ($X^3$=Ac, $Y^3$=OH) through the procedure given in Example 1e above, there is obtained 1α-hydroxy-19-nor-vitamin $D_2$ (IId, $X^1$=$Y^1$=H)

Preparation of Secosterol Compounds

The secosterol of structure III where $R_{12}$ is hydrogen can be prepared according to the method of Lam et al as published in Steroids 26, 422 (1975), the description of which is specifically incorporated herein by reference. The secosterols of structure III, where $R_{12}$ is methyl, ethyl or propyl, can be prepared according to the general process illustrated and described in U.S. Pat. No. 4,800,198 issued Jan. 24, 1989 entitled "Method of Inducing the Differentiation of Malignant Cells With Secosterol", the description of which is specifically incorporated herein by reference.

In accordance with the present invention, the above side chain saturated and unsaturated 1α-hydroxyvitamin D homolog compounds together with the above 19-nor-vitamin D compounds and secosterol compounds are employed in compositions, formulations thereof and methods of using the same for the treatment of such skin conditions as dry skin (lack of dermal hydration), undue skin slackness (i.e., insufficient skin firmness) and insufficient sebum secretion. The compositions are also effective in the general preservation, conditioning and protecting of the skin, e.g., against wrinkles.

Compositions for use in the above-mentioned treatment of skin comprise an effective amount of one or more side chain unsaturated or side chain saturated 1α-hydroxyvitamin D homolog compound, one or more 19-nor-vitamin D compound, or one or more secosterol compound as the active ingredient, and a suitable carrier. An effective amount of such compounds for use in accordance with this invention is from about 0.001 μg to about 10.0 μg per gm of composition, and may be administered orally or parenterally in dosages of from about 0.1 μg/day to about 25 μg/day. A concentration of 0.01 μg per gm of the composition is preferred.

The compositions of this invention are formulated preferably as creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers and antioxidants may also be included as well as agents imparting color or fragrance if desired.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

One or more additional substances which have therapeutic effects on the skin may also be incorporated in the compositions. Thus in one embodiment of this invention the composition also contains one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1% again both by weight based on the weight of the composition. Other suitable types of additional active ingredients which may be incorporated in the compositions of this invention include other compounds known to have a beneficial effect on skin. Such compounds include retinoids such as Vitamin A, in an amount of about 0.003%–0.3% by weight and chromanols such as Vitamin E or a derivative thereof in an amount of about 0.1–10% by weight, both based on the weight of the composition.

Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

Topical application, intraperitoneal injection and oral administration of compositions of this invention was found to be cosmetically effective in field studies. In a typical example, topical application of a lotion containing 0.01 μg of a 1α-hydroxyvitamin D homolog compound per gram of lotion to the skin of nude mice for five weeks resulted in improved skin condition.

Cosmetic Efficacy of 1α-hydroxyvitamin D Compounds

The cosmetic efficacy of compositions containing 1α-hydroxyvitamin D homolog compounds in accordance with this invention was determined by the following procedures:

Two treatment groups of six mice each were available with Group I being controls and Group II behind the treatment group with Trihomo-$D_3$. Three mice in each group received the treatment topically (t) and three mice received it intraperitoneally (ip) three times a week for about 5 weeks. By visual evaluation, the mice treated with the Trihomo-$D_3$ compound (b) had the pinkest, smoothest skin as compared to the control mice.

Replicas were made about 48 hours after the last treatment of the backs of 5 control animals and 4 experimental animals. Silflo™ silicone rubber was spread onto the rear half of each mouse back (anesthetized with diethyl ether) and allowed to polymerize for 5 to 7 minutes. These silicone rubber "negative" replicas were stored in glassine envelopes until polyethylene "positive" replicas were made. The procedures for preparing both the negative and the positive replicas will hereinafter be described.

The nine positive replicas were coated with about 60 nm gold and examined in a JEOL JSM-35C scanning electron microscope at 15 kV accelerating voltage. Differences between replicas were evident to the unaided eye and from Polaroid micrographs made of each replica at X12 to form a montage of the entire surface. Micrographs were also made at X100 and X200 to differentiate fine details of skin surface condition.

Figure 2:
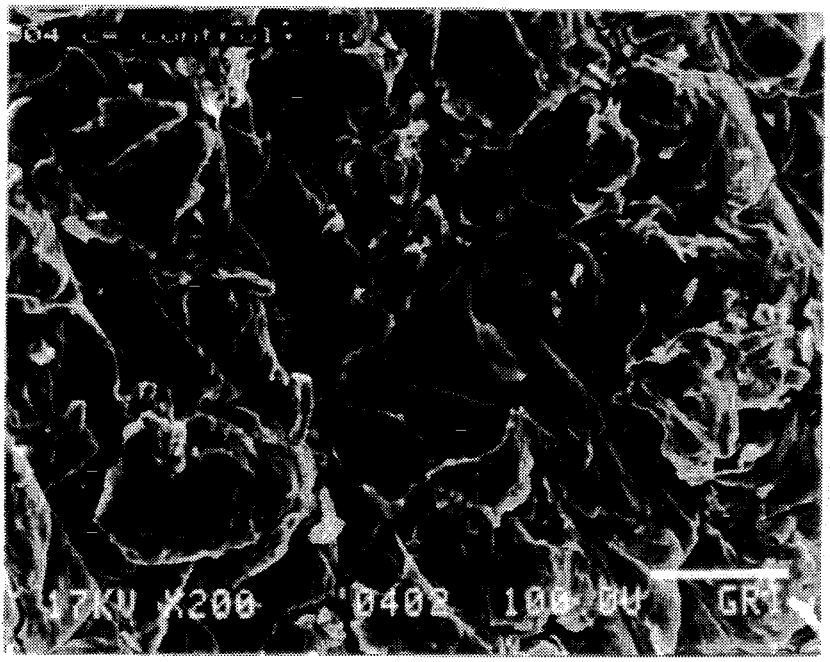
FIG. 2 is a photomicrograph at X200 magnification of a skin replica of a second control mouse treated intraperitoneally with a propylene glycol control vehicle.
Figure 3:
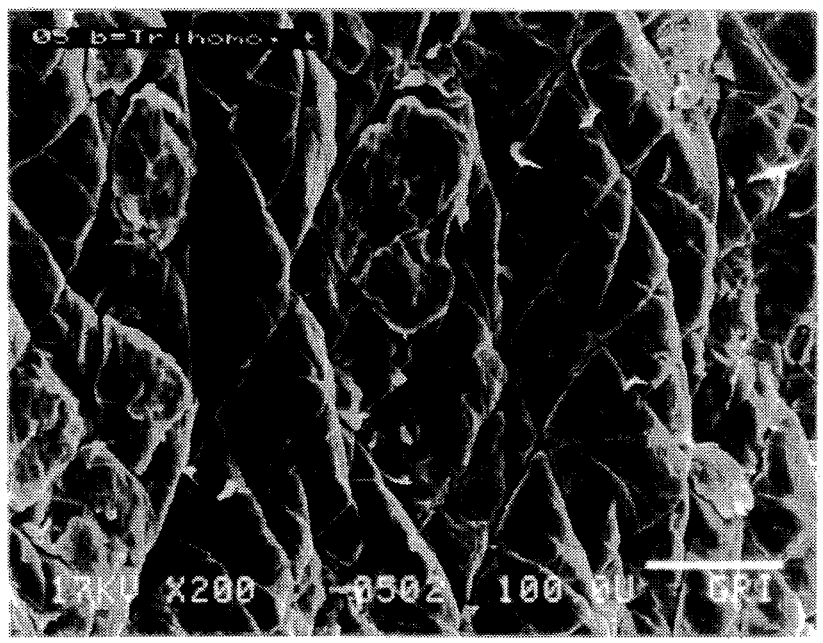
FIG. 3 is a photomicrograph at X200 magnification of a skin replica of an experimental mouse treated topically with $\Delta^{22}$, 24, 24, 24-trihomo-1α,25-dihydroxyvitamin $D_3$.
Figure 4:
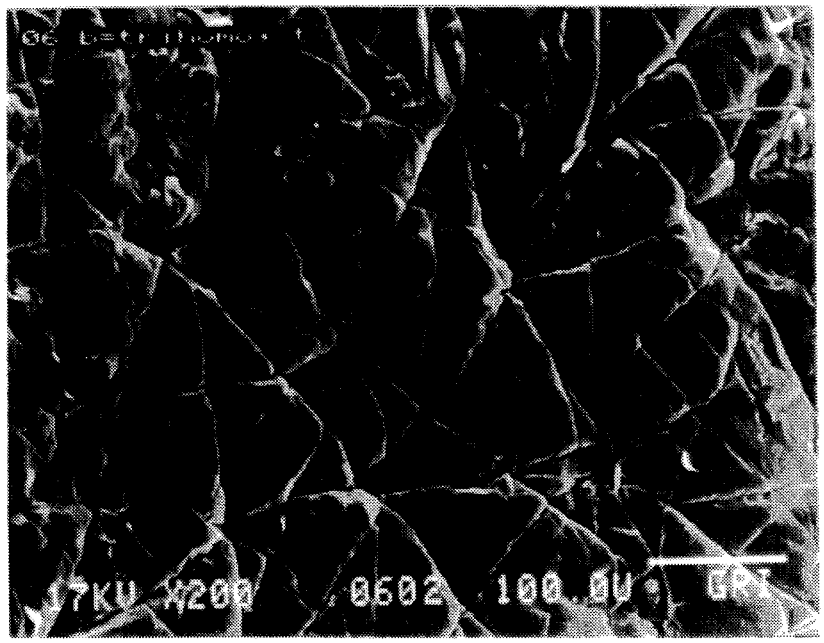
FIG. 4 is a photomicrograph at X200 magnification of a skin replica of a second experimental mouse treated topically with $\Delta^{22}$, 24, 24, 24-trihomo-1α, 25-dihydroxyvitamin $D_3$.
Figure 5:
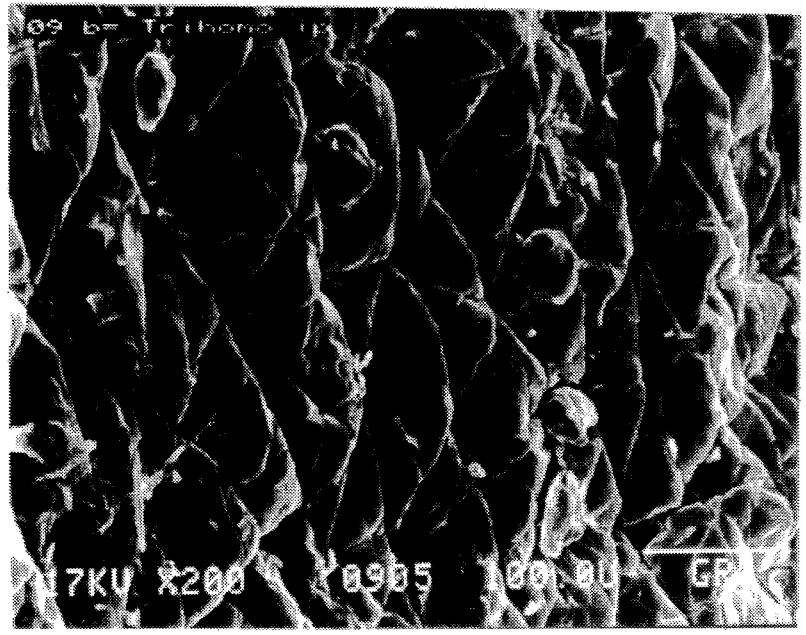
FIG. 5 is a photomicrograph at X200 magnification of a skin replica of an experimental mouse treated intraperitoneally with $\Delta^{22}$, 24, 24, 24-trihomo-1α, 25-dihydroxyvitamin $D_3$.
Figure 6:
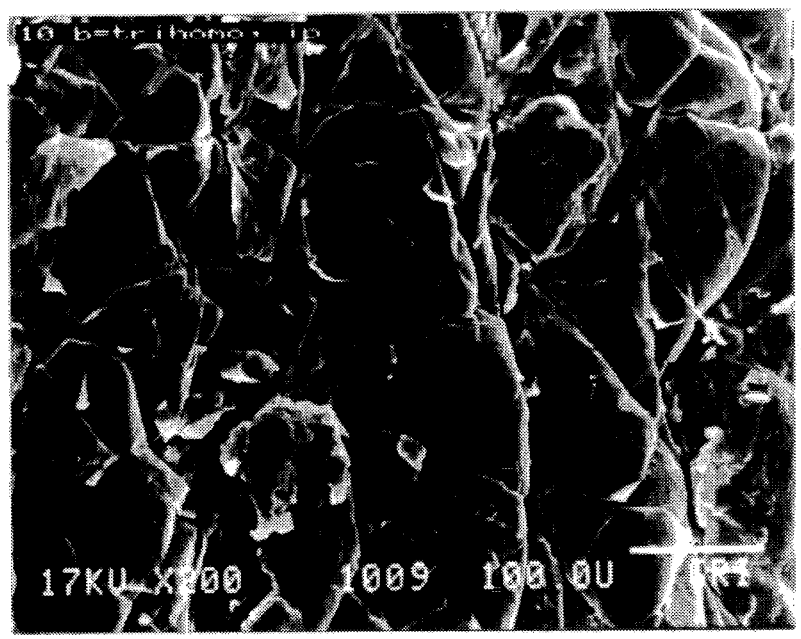
FIG. 6 is a photomicrograph at X200 magnification of a skin replica of a second experimental mouse treated intraperitoneally with $\Delta^{22}$, 24, 24, 24-trihomo-1α,25-dihydroxy vitamin $D_3$.

FIGS. 1 and 2 illustrate the skin surface condition of two of the control mice treated topically and intraperitoneally with a propylene glycol vehicle only. FIGS. 3 and 4 illustrate the skin condition of two of the experimental mice treated topically with $\Delta^{22}$, 24, 24, 24-trihomo-1α, 25-dihydroxyvitamin $D_3$ (Trihomo $D_3$), whereas FIGS. 5 and 6 illustrate the skin condition of two of the experimental mice treated intraperitoneally with $\Delta^{22}$, 24,24,24-trihomo-1α,25-dihydroxyvitamin $D_3$.

The results of the above experiments were that the low magnification (X12) montages of the nine skin replicas could be ranked into four groups according to visible wrinkling and overall skin surface roughness. The best skin condition (rank 1) was exhibited by samples #5, #6 and #8 all of which were treated with Trihomo-$D_3$. The next best was #7. The third rank included three of the control samples. The remaining two controls could placed alone in a fourth rank having the roughest skin (Table 1).

Details of the skin surface such as stratum corneum desquamation, scaling, size and plumpness of skin divisions, were visible on higher magnification (X100 and X200) micrographs and used to rank the replicas from 1=best skin to 6=worst skin (Tables 1 and 2). The treated samples ranked 1 to 4, and the five controls ranked 5 and 6. The top-ranked four included all of the Trihomo-$D_3$ samples (#5, #6, #7, #8). There was no discernible difference between topical and intraperitoneal Trihomo-$D_3$, i.e. #6, #7, #8 were very nearly equal in appearance.

As a result of these experiments, it may be concluded that topical and intraperitoneal treatments of nude mice with 1α-hydroxy Vitamin D analogs produce visible changes in skin surface condition as seen on replicas. Treated samples showed less gross wrinkling and scaling and more smooth, plump, rounded skin microtopography than the respective controls. Treatment with Trihomo-$D_3$ clearly had a greater effect than no treatment at all. Topical treatment could not be differentiated from intraperitoneal treatment.

The visible changes in skin surface condition (as shown in FIGS. 3–6 versus FIGS. 1–2), is in marked contrast with that of compositions containing ergocalciferol or cholecalciferol. Topical application of compositions containing ergocalciferol, for instance, were of low cosmetic efficacy and in fact resulted in decreased skin elasticity (See Table I in Dikstein et al U.S. Pat. No. Re. 33,107). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Further, the compounds of the present invention demonstrated no expected or observed side effects.

TABLE 1

SEM OF MOUSE SKIN REPLICAS

| No. | Treatment | Rank* (×12) | Rank* (×100,200) |
|---|---|---|---|
| #1 | c-t control | 3 | 6 |
| #2 | c-t control | 4 | 6 |
| #3 | c-t control | 3 | 6 |
| #4 | c-ip control | 3 | 6 |
| #5 | b-t Trihomo-$D_3$ | 1 | 4 |
| #6 | b-t Trihomo-$D_3$ | 1 | 1 |
| #7 | b-ip Trihomo-$D_3$ | 2 | 2 |
| #8 | b-ip Trihomo-$D_3$ | 1 | 3 |
| #9 | c-ip control | 4 | 5 |

Treatments:
b = Trihomo-$D_3$
c = Control, vehicle only
t = topical, 160 ng Trihomo-$D_3$/20 μl propylene glycol applied 3 times per week
ip = intraperitoneal, 50 ng Trihomo-$D_3$/50 μl propylene glycol given 3 times per week

TABLE 2

RANKING OF MOUSE SKIN REPLICAS

| No. | Treatment | Rank@(×12) |
|---|---|---|
| 1 | #6 b-t | 1 |
| 2 | #7 b-ip | 2 |
| 3 | #8 b-ip | 1 |
| 4 | #5 b-t | 1 |
| 5 | #9 c-ip | 4 |
| 6 | #1 c-t | 3 |
| 6 | #2 c-t | 4 |

TABLE 2-continued

RANKING OF MOUSE SKIN REPLICAS

| No. | Treatment | Rank@(×12) |
| --- | --- | --- |
| 6 | #3 c-t | 3 |
| 6 | #4 c-ip | 3 |

*Scanning electron micrographs at ×100 and ×200 were judged for skin condition and ranked, with 1 = best (smoothest, plumpest, least scaling) and 6 = worst (roughest, most scaling).
@Photo montages at ×12 magnification were made of each 25 mm diameter replica and ranked for skin condition, with 1 = best (smoothest) and 4 = worst (roughest, more wrinkled).
Treatments:
b = Trihomo-$D_3$
c = Control, vehicle only
t = topical
ip = intraperitoneal Cosmetic Efficacy of 19-nor-vitamin D Compounds Topical application and intraperitoneal injection of cosmetic compositions of 19-nor-vitamin D compounds of this invention was found to be cosmetically effective in field studies. In a typical example, topical application of a lotion containing 0.01 μg of a 19-nor-vitamin D compound per gram of lotion to the skin of nude mice three times per week for five weeks resulted in improved skin condition.

The cosmetic efficacy of compositions containing 19-nor-vitamin D compounds in accordance with this invention was determined by the following procedures:

Two treatment groups of seven mice each were available with one group being controls, and the other group being the treatment group with 1α,25-dihydroxy-19-nor-vitamin $D_3$. The mice in the control group were further defined as Group 1 which contained four mice treated topically (t) only with a propylene glycol vehicle, and Group 2 which contained three mice treated intraperitoneally (ip) only with a propylene glycol vehicle three times a week for 5 weeks. The mice in the treatment group were further defined as Group 3 which contained three mice treated topically (t) with 19-nor-1α,25-dihydroxy-vitamin $D_3$, and Group 4 which contained four mice treated intraperitoneally (ip) with 19-nor-1α,25-dihydroxy-vitamin $D_3$ three times a week for five weeks.

Replicas were made about 48 hours after the last treatment of the backs of two mice from each group, i.e. four control animals and four experimental animals. Silflo™ silicone rubber was spread onto the rear half of each mouse back (anesthetized with diethyl ether) and allowed to polymerize for 5 to 7 minutes. These silicone rubber "negative" replicas were stored in glassine envelopes until polyethylene "positive" replicas were made. The procedures for preparing both the negative and positive replicas will hereinafter be described.

The eight positive replicas were coated with about 60 nm gold and examined in a JEOL JSM-35C scanning electron microscope at 15 kV accelerating voltage. Differences between replicas were evident to the unaided eye and from Polaroid micrographs made of each replica at X30 to form a montage of the entire surface. Micrographs were also made at X1000 and X2000 to differentiate fine details of skin surface condition.

Figure 11:
FIG. 11 is a photomicrograph at X2000 magnification of a skin replica of an experimental mouse treated topically with 1α,25-dihydroxy-19-nor-vitamin $D_3$.
Figure 12:
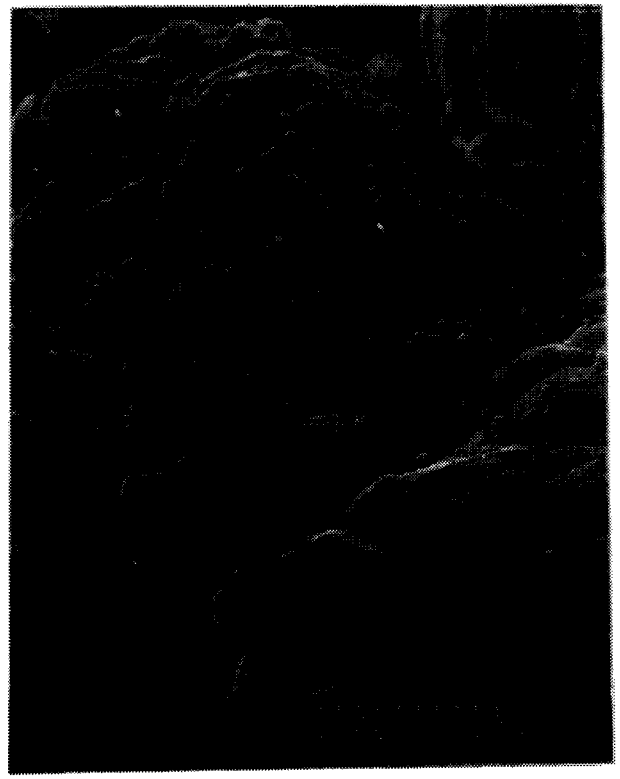
FIG. 12 is a photomicrograph at X1000 magnification of a skin replica of a second experimental mouse treated topically with 1α,25-dihydroxy-19-nor-vitamin $D_3$.
Figure 13:
FIG. 13 is a photomicrograph at X2000 magnification of a skin replica of an experimental mouse treated intraperitoneally with 1α,25-dihydroxy-19-nor-vitamin $D_3$.
Figure 14:
FIG. 14 is a photomicrograph at X1000 magnification of a skin replica of a second experimental mouse treated intraperitoneally with 1α,25-dihydroxy-19-nor-vitamin $D_3$.

FIGS. 1 and 2 illustrate the skin surface condition of two of the control mice treated topically and intraperitoneally with a propylene glycol vehicle only. FIGS. 11 and 12 illustrate the skin condition of two of the experimental mice treated topically with 1α,25-dihydroxy-19-nor-vitamin $D_3$ whereas FIGS. 13 and 14 illustrate the skin condition of two of the experimental mice treated intraperitoneally with 1α,25-dihydroxy-19-nor-vitamin $D_3$.

The results of the above experiments were that the low magnification (X30) montages of the skin replicas could be ranked according to visible wrinkling and overall skin surface roughness. The best skin condition was exhibited by the mice which were treated with 1α,25-dihydroxy-19-nor-vitamin $D_3$. The controls could be placed alone in a rank as having the roughest skin (See Table 3).

Details of the skin surface such as stratum corneum desquamation, scaling, size and plumpness of skin divisions, were also visible on higher magnification (X1000 and X2000) micrographs and used to rank the replicas. The treated samples ranked the best and the controls ranked the worst. The top-ranked skin condition included all of the 19-nor samples. There was no discernible difference between topical and intraperitoneal 19-nor treated samples.

As a result of these experiments, it may be concluded that topical and intraperitoneal treatments of nude mice with 19-nor compounds produce visible changes in skin surface condition as seen on replicas. Treated mice skin showed less gross wrinkling and scaling and more smooth, plump, rounded skin microtopography than the skin of the respective controls. Topical treatment could not be differentiated from intraperitoneal treatment.

TABLE 3

Response of Nude Mice to 19-Nor-1α,25-Dihydroxyvitamin $D_3$

| Group | No. of Animals | Treatment | Observations |
| --- | --- | --- | --- |
| 1 | 4 | Vehicle (Propylene glycol) Topical | Skin remains scaly and wrinkled despite an initial moist appearance. |
| 2 | 3 | Propylene glycol vehicle - given intraperitoneally | Skin scaly and wrinkled. |
| 3 | 3 | 19-nor-1,25-$(OH)_2D_3$ topical in propylene glycol | Within 3 days, skin changed to a pinkish, less wrinkled and more plumpish appearance. Moist appearance continued throughout treatment. |
| 4 | 4 | 19-nor-1,25-$(OH)_2D_3$ given intraperitoneally | After only 3 applications, skin aquired a pink, smoothe appearance with few wrinkles. Skin appeared moisturized. |

I.P. = 50 ng 19-nor-1,25-$(OH)_2D_3$/0.05 ml propylene glycol given 3 times per week
Topical = 100 ng 19-nor-1,25-$(OH)_2D_3$/0.02 ml applied 3 times per week.

The visible changes in skin surface condition (as shown in FIGS. 11–14 versus FIGS. 1–2) is in marked contrast with that of compositions containing ergocalciferol or cholecalciferol. Topical application of compositions containing ergocalciferol, for instance, were of low cosmetic efficacy and in fact resulted in decreased skin elasticity (See Table I in Dikstein et al U.S. Pat. No. Re. 33,107). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Further, since the compounds in accordance with this invention have little or no classical vitamin D activities, no side effects were expected or observed.

Cosmetic Efficacy of Secosterol Compounds

The cosmetic efficacy of compositions containing secosterol compounds in accordance with this invention was determined by the following procedures:

Two treatment groups of six mice each were available with Group I being controls, and Group II being the treatment group with Homo-pregnacalciferol. Three mice in each group received either the control vehicle only or the Homo-pregnacalciferol treatment topically (t) and three mice in each group received either the control vehicle only or the Homo-pregnacalciferol treatment intraperitoneally (ip) three times a week for 5 weeks.

Replicas were made about 48 hours after the last treatment of the backs of 5 control animals and 4 experimental animals. Silflo™ silicone rubber was spread onto the rear half of each mouse back (anesthetized with diethyl ether) and allowed to polymerize for 5 to 7 minutes. These silicone rubber "negative" replicas were stored in glassine envelopes until polyethylene "positive" replicas were made. The procedures for preparing both the negative and positive replicas will hereinafter be described.

The nine positive replicas were coated with about 60 nm gold and examined in a JEOL JSM-35C scanning electron microscope at 15 kV accelerating voltage. Differences between replicas were evident to the unaided eye and from Polaroid micrographs made of each replica at X12 to form a montage of the entire surface. Micrographs were also made at X100 and X200 to differentiate fine details of skin surface condition.

Figure 7:
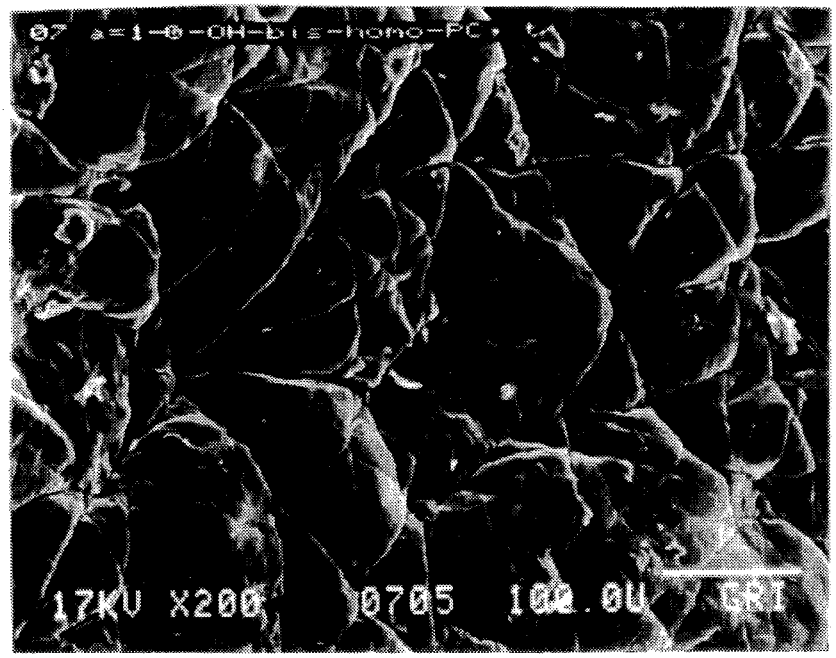
FIG. 7 is a photomicrograph at X200 magnification of a skin replica of an experimental mouse treated topically with 1α-hydroxy-bis-homopregnacalciferol.
Figure 8:
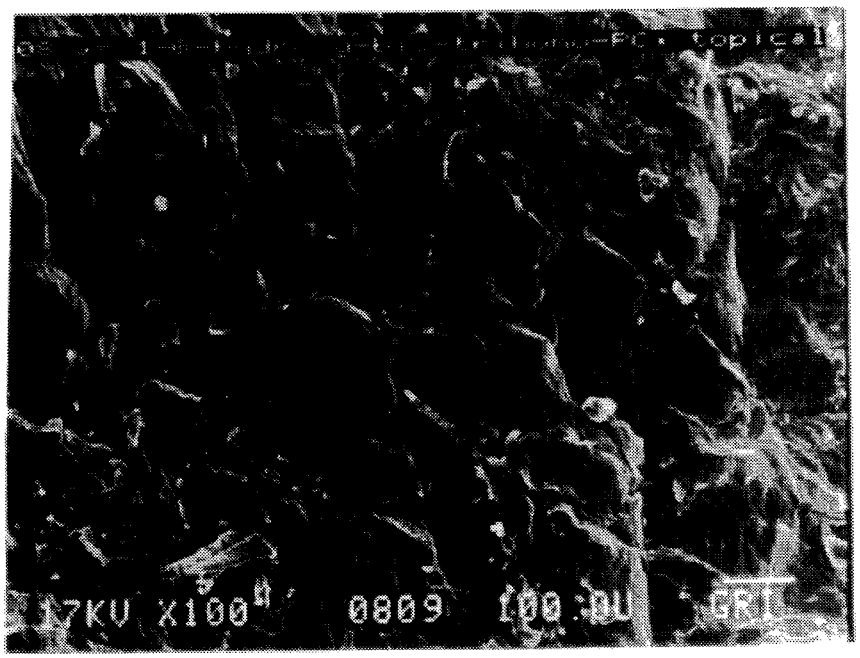
FIG. 8 is a photomicrograph at X200 magnification of a skin replica of a second experimental mouse treated topically with 1α-hydroxy-bis-homopregnacalciferol.
Figure 9:
FIG. 9 is a photomicrograph at X200 magnification of a skin replica of an experimental mouse treated intraperitoneally with 1α-hydroxy-bis-homopregnacalciferol.
Figure 10:
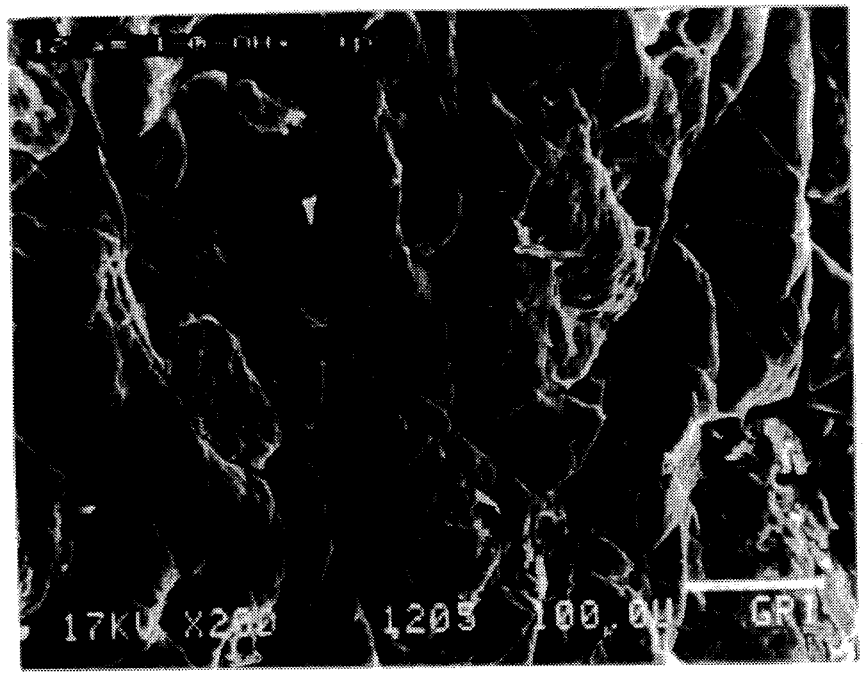
FIG. 10 is a photomicrograph at X200 magnification of a skin replica of a second experimental mouse treated intraperitoneally with 1α-hydroxy-bis-homopregnacalciferol.

FIGS. 1 and 2 illustrate the skin surface condition of two of the control mice treated topically and intraperitoneally with a propylene glycol vehicle only. FIGS. 7 and 8 illustrate the skin condition of two of the experimental mice treated topically with 1α-hydroxy-bis-homo-pegnacalciferol (homo-pregna) whereas FIGS. 9 and 10 illustrate the skin condition of two of the experimental mice treated intraperitoneally with 1α-hydroxy-bis-homo-pregnacalciferol.

The results of the above experiments were that the low magnification (X12) montages of the nine skin replicas could be ranked into three groups according to visible wrinkling and overall skin surface roughness. The best skin condition (rank 1) was exhibited by sample #8 which was treated with Homo-pregna. The next best were #5, #6 and #7 which were all Homo-pregna treatments, but which could not be distinguished at this low magnification with #1 and #3 which were controls. Two controls could be placed alone in a third rank having the roughest skin (See Table 4).

Details of the skin surface such as stratum corneum desquamation, scaling, size and plumpness of skin divisions, were visible on higher magnification (X100 and X200) micrographs and used to rank the replicas from 1=best skin to 6=worst skin (Tables 4 and 5). The treated samples ranked 1 to 4, and the five controls ranked 5 and 6. The top-ranked four included all of the Homo-pregna samples (#5, #6, #7 and #8). There was no discernible difference between topical and intraperitoneal Homo-pregna treated samples, i.e. #5, #6, #7 and #8.

As a result of these experiments, it may be concluded that topical and intraperitoneal treatments of nude mice with secosterol compounds produce visible changes in skin surface condition as seen on replicas. Treated samples showed less gross wrinkling and scaling and more smooth, plump, rounded skin microtopography than the respective controls. Topical treatment could not be differentiated from intraperitoneal treatment.

TABLE 4

SEM OF MOUSE SKIN REPLICAS

| No. | Treatment | Rank* (×12) | Rank*(×100,200) |
|---|---|---|---|
| #1 | c-t control | 2 | 6 |
| #2 | c-t control | 3 | 6 |
| #3 | c-t control | 3 | 6 |
| #4 | c-ip control | 2 | 6 |
| #5 | a-t Homo-pregna | 2 | 2 |
| #6 | a-t Homo-pregna | 2 | 4 |
| #7 | a-ip Homo-pregna | 2 | 3 |
| #8 | a-ip Homo-pregna | 1 | 1 |
| #9 | c-ip control | 2 | 5 |

Treatments:
a = Homo-pregnacalciferol
c = Control, vehicle only
t = topical, 80 ng Homo-pregnacalciferol/20 µl propylene glycol applied 3 times per week
ip = intraperitoneal, 25 ng Homo-pregnacalciferol/50 µl propylene glycol given 3 times per week

TABLE 5

RANKING OF MOUSE SKIN REPLICAS

| No. | Treatment | Rank@×12) |
|---|---|---|
| 1 | #8 a-ip | 1 |
| 2 | #5 a-t | 2 |
| 3 | #7 a-ip | 2 |
| 4 | #6 a-t | 2 |
| 5 | #9 c-ip | 3 |
| 6 | #1 c-t | 2 |
| 6 | #2 c-t | 3 |
| 6 | #3 c-t | 2 |
| 6 | #4 c-ip | 2 |

*Scanning electron micrographs at ×100 and ×200 were judged for skin condition and ranked, with 1 = best (smoothest, plumpest, least scaling) and 6 = worst (roughest, most scaling).
@Photo montages at ×12 mangification were made of each 25 mm diameter replica and ranked for skin condition, with 1 = best (smoothest) and 3 = worst (roughest, more wrinkled).
Treatments:
a = Homogregnaclaciferol
c = Control, vehicle only
t = topical
ip = intraperitoneal The visible changes in skin surface condition (as shown in FIGS. 7–10 versus FIGS. 1–2) is in marked contrast with that of compositions containing ergocalciferol or cholecalciferol. Topical application of compositions containing ergocalciferol, for instance, were of low cosmetic efficacy and in fact resulted in decreased skin elasticity (See Table I in Dikstein et al U.S. Pat. No. Re. 33,107). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Further, since the compounds in accordance with this invention have little or no classical vitamin D activities, no side effects were expected or observed.

The skin replication techniques utilized in preparing the "negative" and "positive" replicas in order to perform the above described experiments and the photomicrographs of FIGS. 1–14 will now be described.

A. SILFLO NEGATIVE REPLICAS

1. Mix Silflo well before dispensing. Put Silflo into plastic syringe, 5 or 10 ml size.

2. Measure out 0.4 to 0.8 ml onto glassine paper or small weighing dish. The amount depends on the area to be replicated and the rate of polymerization desired.

3. Add 1 drop thinner per 0.4 ml Silflo. (Steps 1–3 can be done in advance.)

4. Place TCOM adhesive ring on skin site(s) to be replicated. (This ring was omitted on the mice.)

5. Add 1 drop catalyst per 0.4 ml Silflo and start timer. These amounts can be adjusted if replica sets too fast or too slowly. Silflo should not stiffen until about 2 min. after catalyst addition and should set tack-free from about 3 to 3.5 min. after catalyst.

6. Mix thoroughly with spatula tip for 20–25 sec.

6a. To remove air bubbles, place Silflo dish into small vacuum desiccator and evacuate with mechanical pump until silicone rubber foams up once and collapses; remove at once from vacuum and apply to skin. (Elapsed time should be about 1 min. since addition of catalyst.)

7. Spread Silflo mixture quickly onto skin site with spatula.

8. Let Silflo set for a minimum of 5 minutes, without any movement of the subject. Check that the replica has polymerized before proceeding.

9. Peel off the replica and place it in a dust and lint-free container.

B. POLYETHYLENE POSITIVE REPLICAS

1. Allow Silflo replicas to polymerize completely at room temperature, usually overnight, but 6 hours is sufficient.

2. Place replicas in a dish such as glass petri dish, aluminum weighing dish or on a metal tray. Place a shallow brass ring (or other retaining device which serves as a mold for the polyethylene) on the replica. The diameter of the ring mold will depend on the diameter of the SEM specimen carrier being used (usually 15 mm or 25 mm).

3. Place replicas into 160° C. to about 170° C. oven for a short time, about 5 min. This heating of the replicas drives off moisture and other volatiles.

4. Remove replicas from oven. Fill each brass ring mold with polyethylene pellets.

5. Replace replicas in oven and heat until polyethylene has melted completely and covers the replica surface (about 15 min.).

6. Turn oven off, open oven door and allow replicas to cool slowly. Too rapid cooling can cause cracks and artifacts in the polyethylene.

7. When replicas have cooled almost to room temperature, they can be removed from the oven. Peel off the Silflo replica from the polyethylene replica, which remains within its metal ring.

8. The hardened polyethylene replica can be sputter-coated with gold and examined in the SEM without removing it from its brass ring mold. The replica can also be pushed out of the ring mold and replaced in it again, if necessary.

We claim:

1. A method for treating skin conditions selected from the group consisting of lack of adequate skin firmness, wrinkles, lack of dermal hydration and insufficient sebum secretion which comprises administering to a patient by oral or parenteral means and effective amount of a compound of the formula:

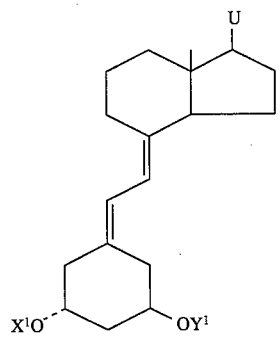

where $X^1$ and $Y^1$ are each selected from the group consisting of hydrogen, acyl, alkylsilyl and alkoxyalkyl, and where U is selected from the group consisting of alkyl, hydrogen, hydroxyalkyl, fluoroalkyl and a side chain of the formula

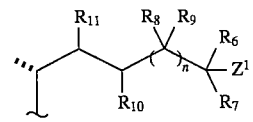

wherein $Z^1$ represents hydrogen, hydroxy or O-acyl, $R_6$ and $R_7$ are each selected from the group consisting of alkyl, hydroxyalkyl and fluoroalkyl, or, when taken together represent the group $-(CH_2)_m-$ where m is an integer having a value of from 2 to 5, $R_8$ is selected from the group consisting of hydrogen, hydroxy, fluorine, O-acyl, alkyl, hydroxyalkyl and fluoroalkyl, $R_9$ is selected from the group consisting of hydrogen, fluorine, alkyl, hydroxyalkyl and fluoroalkyl, or, $R_8$ and $R_9$ taken together represent double-bonded oxygen or double-bonded carbon, $R_{10}$ and $R_{11}$ are each selected from the group consisting of hydrogen, hydroxy, O-acyl, fluorine and alkyl, or, $R_{10}$ and $R_{11}$ taken together form a carbon-carbon double bond or a carbon-carbon triple bond, and wherein n is an integer having a value of from 1 to 5 and wherein the carbon at any one of positions 20, 22, or 23 in the side chain may be replaced by an O, S, or N atom.

2. The method of claim 1 wherein the compound is 1α, 25-dihydroxy-19-nor-vitamin $D_3$.

3. The method of claim 1 wherein the compound is 1α-hydroxy-19-nor-vitamin $D_3$.

4. The method of claim 1 wherein the compound is 1α, 25-dihydroxy-19-nor-vitamin $D_2$.

5. The method of claim 1 wherein the compound is 1α-hydroxy-19-nor-vitamin $D_2$.

6. The method of claim 1 wherein the compound is 1α-hydroxy-19-nor-24 epi-vitamin $D_2$.

7. The method of claim 1 wherein the compound is 1α,25-dihydroxy-19-nor-24 epi-vitamin $D_2$.

8. The method of claim 1 wherein said effective amount comprises about 0.1 μg/day to about 25 μg/day of said compound.

* * * * *